United States Patent

Brands et al.

[11] Patent Number: 6,005,124
[45] Date of Patent: Dec. 21, 1999

[54] METHOD FOR THE PREPARATION OF STEROID DERIVATIVE KETAL

[75] Inventors: Franciscus Theodorus Leonardus Brands, ZA Haren; Pieter Vrijhof, BX Berghem, both of Netherlands

[73] Assignee: Akzo Nobel, N.V., Arnhem, Netherlands

[21] Appl. No.: 09/224,987

[22] Filed: Jan. 4, 1999

Related U.S. Application Data

[63] Continuation of application No. 08/753,135, Nov. 20, 1996, abandoned.

[30] Foreign Application Priority Data

Nov. 30, 1995 [NL]  Netherlands ............... 1001787

[51] Int. Cl.$^6$ .................................................. C07J 21/00
[52] U.S. Cl. ............................................................ 552/34
[58] Field of Search ................................................ 540/34

[56] References Cited

FOREIGN PATENT DOCUMENTS

95/04536   2/1995   WIPO .

OTHER PUBLICATIONS

Hoock et al., "Experimental and theoretical investigations of regioselective ketalization of estra–4,9–diene–3,17–dione." J. Prakt. Chem. vol. 337, pp. 358–362, 1995.

Primary Examiner—Jose' G. Dees
Assistant Examiner—Barbara Badio
Attorney, Agent, or Firm—Mary E. Gormley

[57] ABSTRACT

The invention relates to a method for the preparation of a steroid derivative ketal of formula I:

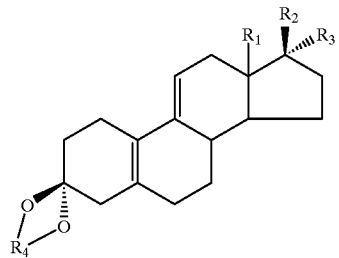

characterized in that a compound of formula II:

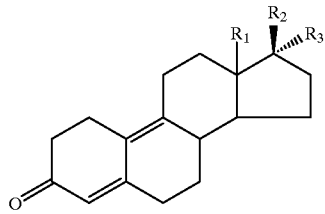

is treated with an alcohol in the presence of an orthoester, wherein $R_1$, $R_2$, $R_3$ and $R_4$ are as defined by the specification.

5 Claims, No Drawings

METHOD FOR THE PREPARATION OF STEROID DERIVATIVE KETAL

This application is a continuation of application Ser. No. 08/753,135, filed Nov. 20, 1996, now abandoned.

The invention relates to a method of the preparation of a steroid derivative ketal.

A steroid-derivative ketal according to this invention is disclosed in German Patent Application DD-296931. According to this method a gonadiene-derivative is treated with an alcohol under the addition of a silylhalogenide as a catalyst. This method is used for the preparation of methyl-, ethyl- and propylketals of 3-keto-5(10),9(11)-gonadiene-derivatives. This method was an improvement of the prior art of that time because the preparation of dialkyl ketals according to the used method (such as reaction of a 3-keto-gonadiene-derivative with an alcohol in the presence of an acid) leads to a product, which under the conditions used, is unstable and which partially decomposes under isolation or drying. To attain the keto in a stable form it should first be neutralized with alkaline which has the disadvantage that in the next step an excess of alkaline must be removed again.

As an intermediate in the synthesis of steroids with progestagenic activity in particular for the use thereof in contraception and hormone supply therapy for peri- en postmenopausal women, there is a need for a good process for the preparation of ketals, in particular cyclic ketals of certain steroid derivatives. The method as disclosed in DD-296931, however, appeared to be unsuitable for an economically acceptable production of ketals.

The yields obtained with this method for the preparation of cyclic 3-ethylene ketal of estra-4,9-diene-3,17-dione were usually between 50 and 65%, with exceptional high flyers of about 75%. Moreover, in this case considerable amounts (up to 50%)) of the unwanted 3,17-diketal were formed.

There is a need for a method of the preparation of ketals, in particular of cyclic ketals of 3-keto-5(10),9(11)-steroiddiene derivatives which can be scaled up and which gives a high yield of stable ketals and which does not lead to the formation of diketals, in the case of 3,17-diketo-steroid derivatives.

The process of this invention for the preparation of a steroid-derivative ketal according the general formula I:

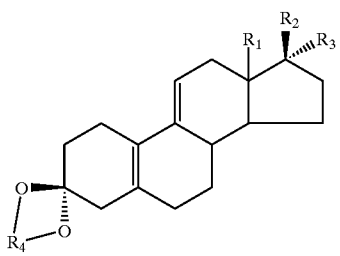

wherein $R_1$ is $CH_3$ or $C_2H_5$;

$R_2$ is OH;

$R_3$ is H, $CH_3$; C≡CH, $CH_2Hal$, or $CH_2CN$; or $R_2$ and $R_3$ together are O;

$R_4$ is (2–5C) alkylene; and

Hal is Cl, Br or I, characterized in that the compound of formula II:

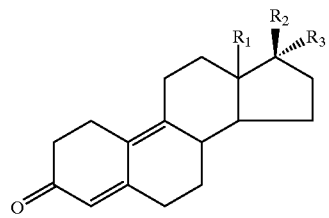

wherein $R_1$, $R_2$ and $R_3$ have the previously given meanings, is treated in the presence of an orthoester of formula III:

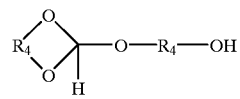

wherein $R_4$ is (2–5C) alkylene or an orthoester of formula IV:

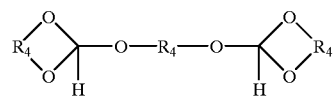

wherein $R_4$ has the previously indicated meaning or a mixture thereof with an alcohol according to the general formula $HOR_4OH$, wherein $R_4$ has the previously given meaning, yields a method which meets the above mentioned requirements.

Preferably $R_4$ is 1,2-ethanediyl, 1,3-propanediyl or 2,2-dimethyl-1,3-propanediyl.

The alcohol according to general formula $HOR_4OH$ can also be prepared in situ by starting with a precursor which gives the free alcohol under the reaction conditions. The ketalisation is generally performed under the usual acidic conditions.

The process can be used specifically for the preparation of a ketal according to formula I wherein $R_1$ is $CH_3$, $R_2$ and $R_3$ are together O, and $R_4$ is —$CH_2$—$CH_2$—.

This product is extremely suitable as and intermediate for the preparation of the progestagenic dienogest.

The term (2–5C) alkylene means an alkylene group having 2 to 5 carbon atoms, such as ethylene, propylene, 2,2-dimethylpropylene and the like.

The term lial means a halogen such as chlorine, bromine or iodine. Chlorine is preferred.

The orthoesters are applied as waterscavenger. Suitable orthoesters are 2,2'-[1,2-ethanediylbis(oxy)-bis-1,3-dioxolane, 2,2'-[1,3-propanediyibis(oxy)]-bis-1,3 dioxane and 2,2'-[2,2-dimethyl-1,3-propanediyl)bis(oxy)]-bis-(5,5-dimethyl)-1,3 dioxane or mixtures thereof. These orthoesters are easily prepared by methods known in the art, for instance by heating a trialkylorthoformate, such as trimethyl- or triethylorthoformate, with a diol, such as ethyleneglycol. The use of the above mentioned orthoesters causes the reaction to proceed at a constant rate resulting in a lower amount of contaminating products.

The invention further relates to a method to a preparation of a compound of formula I, wherein $R_1$, $R_2$, $R_3$, and $R_4$ and Hal have the previously given meanings, characterized in that:

a. a compound with the general formula V:

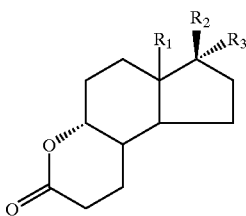

wherein $R_1$, $R_2$ and $R_3$ have the previously given meanings is condensed with a compound of the formula $CH_3-C(OR_4O)-(CH_2)_3-XHal$, wherein $R_4$ and Hal have the previously given meanings and X is a metal atom, in particular magnesium.

b. the hydroxy group of the product obtained is oxidized in the usual manner
c. is ringclosed under alkaline conditions
d. the ketal is cleaved under acidic conditions
e. after which under alkaline conditions is ringclosed to a compound with formula II wherein $R_1$, $R_2$ and $R_3$ have the previously given meanings
f. after which the product obtained is treated according to the above described method of ketalisation.

The advantage of this process is that inexpensive starting tools are used and that the oxidation estate of the formed steroid A- and B-ring is the correct one. This process is of particular advantage for the preparation of suitable intermediates for the preparation of dienogest. In that case the process starts with compounds according to general formula IV wherein $R_1$ is $CH_3$, and $R_2$ and $R_3$ together are O.

The usual manners to oxidize the hydroxy group are methods as disclosed in handbooks and which are clear for the person of ordinary skill. Examples of suitable oxidation methods are the treatment with chromiumoxyde/pyridine, chlorine/pyridine, calciumdichromate, pyridinechromates and N-bromosuccinimide, and the Oppenauer oxidation.

The ringclosure of reaction step e. occurs under alkaline conditions, which condition in principle can be obtained with each reagent. In particular suitable is treatment with potassium-tert-butylate.

The invention further relates to a process for the preparation of the compound according to formula II wherein $R_1$ is $CH_3$, $R_2$ is OH, and $R_3$ is $CH_2Hal$ or $CH_2CN$, characterized in that the 17-keto group of the ketal steroid derivatives according to formula I is converted into a 17-spiro-oxirane group, after which the oxirane group is opened by treatment with a halogenide or cyanide, after which the ketal group of the reaction product obtained is cleaved under acidic conditions.

The conversion to the 17-spiro-oxirane can be performed in the usual manner to prepare 17-spiro-oxirane steroid derivatives, for example according to the method of Ponsold et al., Pharmazie 33 (1978), 792 with trimethylsulphoniumiodide and potassium-tert-butylate. Other suitable methods are treatments with trimethylsulphoxonium iodide and potassium-tert-butylate. As a base also sodium hydride, lithium amide or sodium methoxyde in solvents as dimethylformamide, tetrahydrofuran and dimethylsulphoxide can be used.

The ringopening of the oxirane ring is performed with a halogenide or cyanide. Preferably a potassium or sodium halogenide or cyanide is used as halogenide or cyanide. As haloqenide preferably potassium- or sodium iodide is used. A suitable method is disclosed in the above mentioned Ponsold reference.

The cleavage of the ketal can be performed in the usual manner with acids in suitable solvents. Examples are hydrochloric acid, sulphuric acid and the like in alcohols, ketones (for instance acetone) ethyl acetate and the like, possibly mixed with water.

The invention finally relates to the synthesis of compounds according to formula II, wherein $R_1$ is $CH_3$, $R_2$ is OH, and $R_3$ is $CH_2Hal$ or $CH_2CN$, characterized in that starting with the compound with formula V by using the above described method through the ketalization of the compound of formula II to the compound with formula I which is converted according to the above described method into the compound with formula II wherein $R_1$ is $CH_3$, $R_2$ is OH, and $R_3$ is $CH_2Hal$ or $CH_2CN$.

The invention is further illustrated by the following examples.

EXAMPLE 1

(+)-5α-Hydroxy-7aβ-methyl-4α-[7,7-(dimethylpropylenedioxy)-3-oxo-octyl]-2,3,3aα,4,5,6,7,7a-octahydro-1H-inden-1-one 1,2-dibromomethane (3.2 g) is added to a mixture of 19.6 g magnesium shavings and 105 ml of dry ethylether at 22° C. After starting the reaction the temperature raised to about 32° C. and development of gas occurred. The mixture was stirred for another 30 minutes. A mixture of 17.5 g 5-chloro-2-pentanone-neopentylacetal and 3.2 g of 1,2-dibromomethane was added to the reaction mixture in about 30 minutes under slowly stirring. The temperature raised to reflux (about 36° C.). The mixture was stirred for another 15 minutes. A mixture of 132.7 g 5-chloro-2-pentanone-neopentylacetal and 105 ml of tetrahydrofuran was added to the reaction mixture in about 2 hours, such that the reaction mixture remained refluxing. The reaction mixture was stirred without heating until the temperature diminished again. 400 ml of tetrahydrofuran were added the reaction mixture in about 1 hour. The Grignard mixture was heated for another 3 hours under reflux and cooled to 20° C. The excess of magnesium was removed and the molarity of the Grignard solution was determined.

750 ml of 0.8 M 2-pentanone-neopentylacetale-5-magnesium chloride solution in tetrahydrofuran was added to a suspension of 126.7 g of (+)-5α-hydroxy-7aβ-methyl-2,3,3aα,4,5,6,7,7a-octahydro-1H-inden-1-one-4α-(3-propionic-acid)-lacton (U.S. Pat. No. 4,784,953, included by reference) at −30° C. in about 2 hours. There was stirred for another 90 minutes at −30° C. The reaction mixture was added to a solution of 525 g ammonium chloride in 525 ml of water at 0° C. in 1 hour. 550 ml of water was added to this mixture. The tetrahydrofuran was distilled of under vacuum under addition of water whereby the pH raised to 7.7. At 50° C. 840 ml of toluene were added and after 30 minutes of stirring the layers were separated. The toluene layer was washed at 50° C. with water and 0.1% of pyridine and 20 g of sodium sulphate were added to the toluene layer which was stirred for 30 minutes at 20° C. The suspension was filtered and 0.1%, v/v of pyridine was added to the filtrate. The netto weight of the toluene solution was determined by a drying residue.

EXAMPLE 2

(+)-3,3-(dimethylpropylendioxy)-4,5-seco-estr-9-ene-5,17-dione 72 g of chlorine gas was introduced in a solution of 236 g of (+)-5α-hydroxy-7aβ-methyl-4α-[7,7-

(dimethylpropylenedioxy)-3-oxo-octyl]-2,3,3a$\alpha$,4,5,-6,7,7a-octahydro-1H-inden-1-one in 1500 ml of toluene and 285 ml of pyridine at 0° C. in 7 to 8 hours. The reaction mixture was stirred for another hour at 0° C. The reaction mixture was poured into a solution of 274 of sodium sulphite and 228 g of sodium carbonate in 2500 ml of water. The layers were separated and the toluene layer was washed with water. A solution of 246 g of potassium hydroxyde in 345 ml of water and 810 ml of methanol were added to the toluene solution. The reaction mixture was stirred for another 2 hours at 65° C. After cooling to 50° C. the layers were separated and the toluene layer was washed at 50° C. using a 50% methanol solution and thereafter water. 375 ml of pyridine were added to the toluene solution and the solution was evaporated to dryness. 1100 ml of ethanol and 4 ml of pyridine were added to the drying residue and this mixture was boiled for 50 minutes. After cooling to 40° C. the solution was treated with active carbine (Norit®). After filtration the ethanol solution was used as such.

EXAMPLE 3

Estra-4,9-diene-3,17-dione

A solution of 100 g of (+)-3,3-dimethylpropylenedioxy-4,5-seco-estr-9-ene-5,17-dione and 18.7 ml of 2N hydrochloride acid in 500 ml of acetone was stirred under nitrogen for 2.5 hours at 23° C. A solution of 4.5 g of sodium acetate in 1120 ml of water was added to the reaction mixture. The acetone was distilled of whereby the volume was kept the same by addition of water. 5% sodium chloride (by volume) and 200 ml of toluene were added at 50° C. The layers were separated and the water layer was extracted with toluene. The collected toluene extracts were washed with 5% sodium chloride solution and evaporated to a volume of 500 ml. This solution was used in the next step.

The toluene solution of (+)-4,5-seco-estr-9-ene-3,5,17-trione was added to a suspension of 8 g potassium-tert-butylate in 240 ml of toluene and 77 ml of tert-butanol under nitrogen at 18° C. This mixture was stirred for another 4.5 hours at 18° C. 8 ml of acetic acid followed by 768 ml of water were added to the reaction mixture. The layers were separated and the toluene layer was washed with 5% sodium chloride solution. The toluene solution was evaporated to a volume of 175 ml and 440 ml of hexane were added. The suspension was boiled during 30 minutes. After cooling there was stirred for 2 hours at 0° C. 66 g of crude of estra-4,9-diene-3,17-dione was obtained after filtration and drying. After purification through a silica column and crystallisation from a mixture of ethylacetate and hexane 40 g of pure estra-4,9-diene-3,17-dione was obtained.

EXAMPLE 4

Estra-5(10),9(11)-diene)-3,17-dione 3,3-ethyleneketal

A mixture of 500 ml of cyclohexane, 183 ml of triethylorthoformate, 92 ml of ethyleneglycol and 0.9 g of p-toluene-sulphonic acid was stirred for 30 minutes at room temperature and thereafter heated to reflux. The formed ethanol was destined of together with cyclohexane whereas the volume was kept constant by addition of cyclohexane. After 4.5 hours the residue of cyclohexane was distilled of and 1 eq. of the residue was added as such as waterscavenger under an atmosphere of nitrogen to 1 g of estra-4,9-diene-3,17-dione, 0.1 eq. of hydrogen chloride in dioxane and 1.5 eq. of ethyleneglycol in 15 ml of dimethoxyethane at −10° C. After 75 min. the reaction mixture was poured into a saturated aqueous solution of sodium hydrogen carbonate. The crystal mass was filtered off after 15 min. of drying, washed with water and dried under vacuum after which 1.1 g of estra-5(10),9(11)-diene-3,17-dione 3,3-ethyleneketal was obtained. After crystallisation from ethanol 1 g of product was obtained having a purity of better than 97%.

EXAMPLE 5

17$\beta$-Spiro-1',2'-oxiran-estra-5(10),9(11)-dien-3-one 3-ethylene ketal

Potassium-t-butylate (32.7 g) was added to a solution of 30.0 g of estra-5(10),9(11)-dien-3,17-dione 3-ethylene ketal and 42.2 g of trimethylsulfonium iodide in 300 ml of dimethylformamide at a temperature $\leq$35° C. The mixture was stirred at about 30° C. for 75 min, after which the reaction mixture was poured slowly in 2.7 liters of water. The aqueous layer was extracted three times with 300 ml of ethyl acetate. The organic layer was washed with water, evaporated to dryness and dried under vacuo at 50° C., to obtain 29.8 g of 17$\beta$-spiro-1',2'-oxiran-estra-5(10),9(11)-dien-3-one 3-ethylene ketal.

EXAMPLE 6

17$\alpha$-Cyanomethy-17$\beta$-hydroxy-estra-5(10),9(11)-dien-3-one 3-ethylene ketal A solution of 64.5 g of potassium cyanide in 129 ml of water was added to a solution of 25.8 g of 17$\beta$-spiro-1',2'-oxiran-estra-5(10),9(11)-dien-3-one 3-ethylene ketal in 645 ml of ethanol. The mixture was stirred for 5 h at 25° C., after which 650 ml of water was added slowly. The mixture was allowed to stand for 15 h, after which the clear solution was decanted from a oily residue. The oily residue was dissolved in 150 ml of ethyl acetate, after which the organic solution was washed with water and evaporated to dryness to obtain 20.2 g of 17$\alpha$-cyanomethyl-17$\beta$-hydroxy-estra-5(10),9(11)-dien-3-one 3-ethylene ketal.

EXAMPLE 7

17$\alpha$-Cyanomethyl-17$\beta$-hydroxy-estra-4,9-dien-3-one (dienogest)

Hydrochloric acid (11.0 ml) was added to a solution of 17.0 g of 17$\alpha$-cyanomethyl-17$\beta$-hydroxy-estra-5(10),9(11)-dien-3-one 3-ethylene ketal in 362 ml of acetone. The mixture was stirred for 2 h at 25° C., after which the mixture was neutralized with 20.8 ml of triethylamine and 110 ml of water was added. Acetone (320 ml) was distilled off and after cooling to 20° C. the crystals were filtered off and dried under vacuum at 50° C. to obtain 13.0 g of crude 17$\alpha$-cyanomethyl-17$\beta$-hydroxy-estra-4,9-dien-3-one. The crude material was crystallized two times from acetone to obtain 7.4 g of 17$\alpha$-cyanomethyl-17$\beta$-hydroxy-estra-4,9-dien-3-one, having a purity $\geq$98%.

We claim:

1. A process for the preparation of a steroid-derivative ketal according to general formula I:

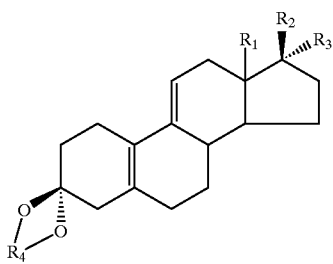

wherein $R_1$ is $CH_3$ or $C_2H_5$;
$R_2$ and $R_3$ together are O;
$R_4$ is (2–5C) alkylene;
the process comprising:
   treating a compound of formula II:

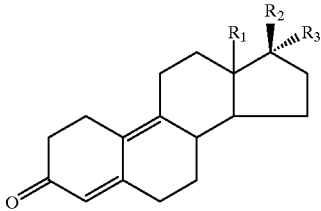

wherein $R_1$, $R_2$ and $R_3$ have the previously given meanings, with an alcohol according to the general formula $HOR_4OH$, wherein $R_4$ has the previously given meaning, in the presence of an orthoester of formula III:

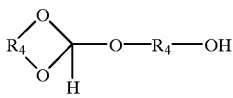

or an orthoester of formula IV:

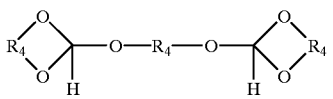

wherein $R_4$ has the previously indicated meaning, or a mixture of said orthoesters.

2. A process according to claim 1 wherein $R_1$ is $CH_3$ and $R_4$ is $-CH_2-CH_2-$.

3. A process according to claim 1 wherein the orthoester is 2,2-[1,2-ethanediylbis(oxy)-bis-1,3-dioxolane, 2,2'-[1,3-propanediylbis(oxy)]-bis-1,3 dioxane and 2,2'-[2,2-dimethyl-1,3-propanediyl)bis(oxy)]-bis-(5,5-dimethyl)-1,3 dioxane or a mixture thereof.

4. A process according to claim 1 for the preparation of a compound of formula I,

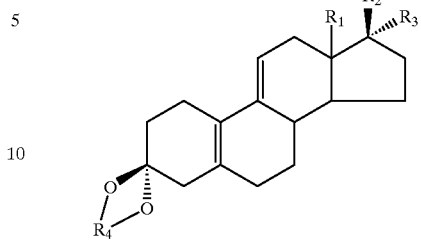

wherein $R_1$, $R_2$, $R_3$, and $R_4$ are defined as in claim 1, comprising, prior to the steps set forth in claim 1:

a. condensing a compound with the general formula V:

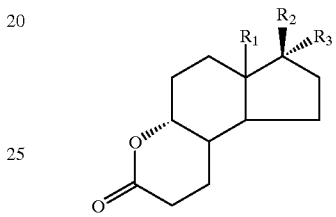

wherein $R_1$, $R_2$ and $R_3$ have the previously given meanings, with a compound of the formula $CH_3-C(OR_4O)-(CH_2)_3-XHal$, wherein $R_4$ has the previously given meaning, Hal is Cl, Br or I, and X is a metal atom;

b. oxidizing the hydroxy group of the product obtained in (a);

c. ringclosing the product obtained in (b) under alkaline conditions;

d. cleaving the ketal of (c) under acidic conditions;

e. after which under alkaline conditions, ringclosing the compound of (d) to a compound with formula II

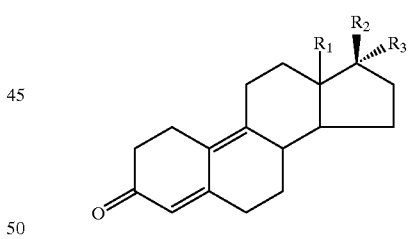

wherein $R_1$, $R_2$ and $R_3$ have the previously given meanings.

5. A process according to claim 4 wherein $R_1$ is $CH_3$.

* * * * *

UNITED STATES PATENT AND TRADEMARK OFFICE
CERTIFICATE OF CORRECTION

PATENT : 6,005,124

DATED : December 21, 1999

INVENTOR(S) : Franciscus Brands et al

It is certified that error appears in the above-identified patent and that said Letters Patent is hereby corrected as shown below:

On the title page, item [56] References Cited, insert the following:

U.S. Patent Documents

| | | |
|---|---|---|
| 4,400,524 | 8/23/83 | Huber |

Foreign Patent Documents

| | | | |
|---|---|---|---|
| WO 95/045336 | 2/18/95 | WO | Peeters et al |
| 1,096,761 | 12/29/67 | Great Britain | Roussel-Uclaf |
| 9200991 | 1/23/92 | PCT | |
| 9504536 | 2/16/95 | PCT | |
| 632347 | 11/1863 | Belgium | |
| 0582338 | 2/9/94 | EPO | |
| 0231671 | 8/12/87 | EPO | |
| 2201287 | 4/26/74 | France | |
| 5435 | 10/9/67 | France | |
| 1096761 | 12/29/67 | Great Britain | |
| 3208432 | 8/15/83 | Germany | |
| 453348 | 6/14/68 | Switzerland | |

UNITED STATES PATENT AND TRADEMARK OFFICE
CERTIFICATE OF CORRECTION

PATENT : 6,005,124

DATED : December 21, 1999

INVENTOR(S) : Franciscus Brands et al

It is certified that error appears in the above-identified patent and that said Letters Patent is hereby corrected as shown below:

Other Documents
C. Hoock et al., *J. Prakt. Chem.*, 337:5:358-362, 1995
C. Mackenzie et al., *Journal of Organic Chemistry*, 20:1695-1701, 1955
B. Mezenbach et al., *Pharmazie*, 39:7:496-497, 1984
A. Liu et al., *Journal of Medicinal Chemistry*, 35:11:2113-2129, 1992
Teutsch et al., "Synthesis of 11beta-vinyl-19-norsteroids". Steroide vol. 39(6), 607-615, 1982.

Signed and Sealed this

Tenth Day of April, 2001

*Attest:*

NICHOLAS P. GODICI

*Attesting Officer*  *Acting Director of the United States Patent and Trademark Office*